United States Patent
Hen et al.

(10) Patent No.: US 8,852,930 B2
(45) Date of Patent: Oct. 7, 2014

(54) IN VIVO GENE REGULATION BY THE COMBINATION OF KNOCK-IN-TETO SEQUENCE INTO THE GENOME AND TETRACYCLINE-CONTROLLED TRANS-SUPPRESSOR (TTS) PROTEIN

(75) Inventors: Rene Hen, Tenafly, NJ (US); Kenji Tanaka, Kanagawa (JP)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/577,281

(22) PCT Filed: Feb. 8, 2011

(86) PCT No.: PCT/US2011/024068
§ 371 (c)(1),
(2), (4) Date: Nov. 20, 2012

(87) PCT Pub. No.: WO2011/100250
PCT Pub. Date: Aug. 18, 2011

(65) Prior Publication Data
US 2013/0061343 A1    Mar. 7, 2013

Related U.S. Application Data

(60) Provisional application No. 61/337,995, filed on Feb. 9, 2010.

(51) Int. Cl.
| | | |
|---|---|---|
| C12N 15/00 | (2006.01) | |
| C12N 5/00 | (2006.01) | |
| C07H 21/00 | (2006.01) | |
| A01K 67/027 | (2006.01) | |
| C12N 15/85 | (2006.01) | |

(52) U.S. Cl.
CPC .......... *C07H 21/00* (2013.01); *A01K 2227/105* (2013.01); *C12N 2800/107* (2013.01); *A01K 67/0275* (2013.01); *A01K 2217/072* (2013.01); *A01K 2217/075* (2013.01); *C12N 2830/003* (2013.01); *C12N 2800/30* (2013.01); *A01K 2217/206* (2013.01); *C12N 15/8509* (2013.01); *C12N 15/85* (2013.01); *A01K 2217/203* (2013.01)
USPC ........................................ 435/320.1; 435/325

(58) Field of Classification Search
None
See application file for complete search history.

(56) References Cited

U.S. PATENT DOCUMENTS

| | | |
|---|---|---|
| 2003/0009780 A1 | 1/2003 | Allen |
| 2006/0212949 A1 | 9/2006 | Alphey |
| 2007/0107075 A1 | 5/2007 | Klein et al. |
| 2009/0113561 A1 | 4/2009 | Von Melchner et al. |
| 2009/0217399 A1 | 8/2009 | Stern et al. |
| 2013/0061343 A1* | 3/2013 | Hen et al. ........................ 800/21 |

FOREIGN PATENT DOCUMENTS

EP    1715051    10/2006

OTHER PUBLICATIONS

Notification of Transmittal of the International Search Report and the Written Opinion of the International Searching Authority, or the Declaration, including an International Search Report and Written Opinion of the International Searching Authority, mailed Apr. 12, 2011 in connection with PCT International Application No. PCT/US2011/024068, filed Feb. 8, 2011.
Tanaka et al. (2010). FAST (Flexible Accelerated STOP TetO-knockin): a versatile and efficient new gene modulating system. *Biol Psychiatry*, 67(8), 770-773.
Gross C et al: "Serotonin1 A receptor acts during development to establish normal anxiety-like behaviour in the adult", Nature: International Weekly Journal of Science (and Supplementary Information), Nature Publishing Group, United Kingdom, vol. 416, No. 6879, Mar. 28, 2002, pp. 396-400, XP002416652, ISSN: 0028-0836, DOI: 10.1038/416396A.
Mao Junhao et al: "An ES cell system for rapid, spatial and temporal analysis of gene function in vitro and in vivo", Nucleic Acids Research, Information Retrieval Ltd, vol. 33, No. 18, Oct. 12, 2005, pp. e155-1, XP002464116, ISSN: 0305-1048, DOI: 10.1093/NAR/GNI146.

* cited by examiner

*Primary Examiner* — Michael Burkhart
(74) *Attorney, Agent, or Firm* — Leason Ellis LLP

(57) ABSTRACT

Disclosed is a FAST (Flexible Accelerated STOP TetO-knockin) system, an efficient method for manipulating gene expression in vivo to rapidly screen animal models of disease. This invention further discloses a single gene targeting event yielding 2 distinct knockin mice—STOP-tetO and tetO knockin—which permit generation of multiple strains with variable expression patterns: 1) knockout, 2) Cre-mediated rescue; 3) tTA-mediated misexpression; 4) tTA-mediated overexpression; and 5) tTS-mediated conditional knockout/knockdown. Using the FAST system, multiple gain- and loss-of-function strains can therefore be generated on a timescale not previously achievable. These strains can then be screened for clinically-relevant abnormalities. The flexibility and broad applicability of the FAST system is demonstrated by targeting several genes encoding proteins implicated in neuropsychiatric disorders: Mlc1, Neuroligin 3, the serotonin 1A receptor, and the serotonin 1B receptor.

12 Claims, 10 Drawing Sheets

Figure 9
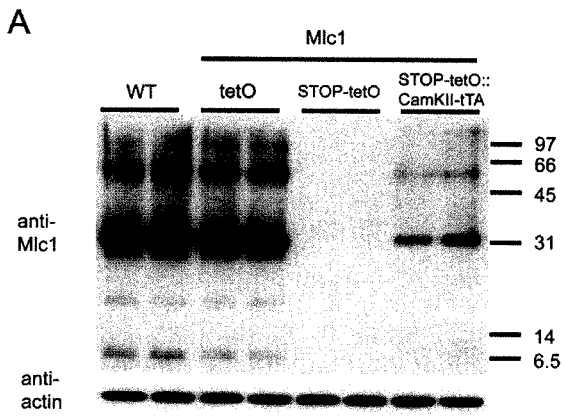
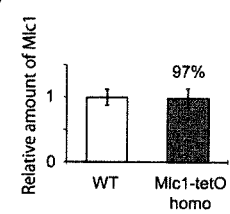
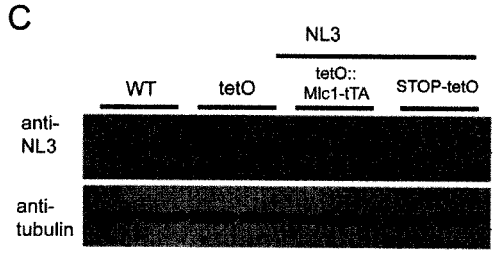
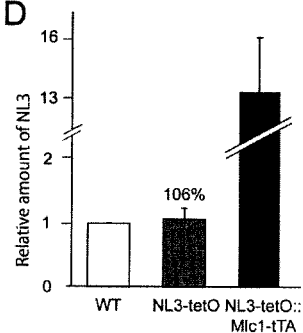

| Brain Region | 5-HT1A Expression | | 5-HT1B Expression | |
|---|---|---|---|---|
| | WT | tetO1A | WT | tetO1B |
| Hippocampus (CA1) | Y | Y | Y | Y |
| Hippocampus (Dentate) | Y | Y | N | N |
| Entorhinal Cortex | Y | Y | Y | Y |
| Amygdala | Y | Y | Y | Y |
| Dorsal Raphe | Y | Y | N | N |
| Hippocampus (CA3) | N | N | N | N |
| Caudoputamen | N | N | Y | Y |
| Nucleus Accumbens | N | N | Y | Y |
| Cerebellum | N | N | Y | Y |
| Substantia Nigra | N | N | Y | Y |
| Superior Colliculus | N | N | Y | Y |

IN VIVO GENE REGULATION BY THE COMBINATION OF KNOCK-IN-TETO SEQUENCE INTO THE GENOME AND TETRACYCLINE-CONTROLLED TRANS-SUPPRESSOR (TTS) PROTEIN

This application is a §371 national stage of PCT International Application No. PCT/US2011/024068, filed Feb. 8, 2011, claiming the benefit of U.S. Provisional Application No. 61/337,995, filed Feb. 9, 2010, the contents of each of which are hereby incorporated by reference in their entirety.

Throughout this application, various publications are referred to by arabic numerals. Full citations for these publications are presented in a References section immediately before the claims. Disclosures of the publications cited in the References section in their entireties are hereby incorporated by reference into this application in order to more fully describe the state of the art as of the date of the methods and apparatuses described herein.

REFERENCE TO SEQUENCE LISTING

This application incorporates-by-reference nucleotide and/or amino acid sequences which are present in the file named "120806_0575_78287_PCT_US_Substitute_Sequence_Listing_GC.txt," which is 4.84 kilobytes in size, and which was created Aug. 3, 2012 in the IBM-PC machine format, having an operating system compatibility with MS-Windows, which is contained in the text file filed Aug. 6, 2012 as part of this application.

The invention disclosed herein was made with government support under National Institute of Health (NIH), NIH/National Research Service Award (NRSA) F30MH083473, The Brain and Behavior Research Fund (NARSAD), and the National Institute of Mental Health (NIMH) research fellowship. Accordingly, the U.S. Government has certain rights in this invention.

BACKGROUND OF THE INVENTION

Gain-of-function and loss-of-function studies are commonly used to examine gene function in vivo, particularly in attempts to model human disease in animals. Developing animal models of disease is key to the process of elucidating neuropsychiatric disease pathophysiology, in turn leading to drug discovery and translation to patient populations. However, these studies typically involve generating separate lines of transgenic mice that over- or under-express the gene of interest, a process that can take several years. Increasing the speed of this screening process is of utmost importance for development of new neuropsychiatric medications based on novel genetic targets.

It is often not possible to predict how changes in candidate gene expression patterns will affect behavior. This is clearly demonstrated by the example of the serotonin transporter (SERT). SERT knockout mice, which have increased levels of serotonin throughout life due to constitutive absence of SERT, demonstrate increased depression-related behavior (1). In contrast, SERT overexpression yields a low-anxiety phenotype (2). These results were not expected since blocking SERT in adulthood with serotonin-reuptake inhibitors leads to decreased depression and anxiety. This example clearly demonstrates the need for empirical determination of effects of changes in gene expression when developing clinically-relevant animal models.

BRIEF SUMMARY OF THE INVENTION

The subject invention provides a targeting vector for in vivo gene regulation in a mammalian cell, wherein the targeting vector introduces the LoxP-FRT-Neo STOP-FRT-tetO-LoxP cassette near a gene of interest thereby allowing controlled expression of said gene.

The subject invention also provides a method of generating transgenic mice having integrated in its genome LoxP-FRT-Neo STOP-FRT-tetO-LoxP cassette near a gene of interest thereby allowing controlled expression of said gene.

The invention also provides a new technological approach for generating several different mouse strains from one single gene-targeting event using the LoxP-FRT-Neo-STOP-FRT-tetO-LoxP cassette.

This invention also provides an approach to optimize screening of mice with variable gene expression patterns to more efficiently find useful disease models.

The invention also provides a system—FAST (Flexible Accelerated STOP TetO-knockin)—to generate mouse models using genes that have been linked to disease, but 1) have unknown function and 2) have not yet been knocked out in mice.

The invention also provides a system—FAST (Flexible Accelerated STOP TetO-knockin)—involving a single gene targeting event using Cre-recombinase, tTA (tetracycline-controlled transcriptional-activator), and tTS (tetracycline-controlled transcriptional-silencer) lines of mice to rapidly produce 5 separate lines of mice from the original knock-in resulting in five versatile applications:
 1) knockout;
 2) Cre-mediated rescue;
 3) tTA-mediated ectopic expression;
 4) tTA-mediated overexpression; and
 5) tTS-mediated conditional knockout/knockdown.

The invention also provides a system—FAST—to easily integrate temporal and spatial specificity into the manipulations of gene expression.

BRIEF DESCRIPTION OF THE FIGURES

FIG. 9. tetO insertion does not affect translation levels in genes with multiple exons: Mlc1 and Neuroligin 3 genes. (A) Western blot data with Mlc1 antibody show two main bands (~30 KDa and ~60 KDa [dimer formation]) from wild type, Mlc1 tetO knock-in homozygote, and αCamKII-tTA::Mlc1 STOP tetO knock-in homozygote, suggesting normal splicing. Cerebellar protein extracts from wild type, Mlc1 tetO knock-in homozygote, and Mlc1 STOP tetO knock-in homozygote and forebrain extract from CamKII-tTA::Mlc1 STOP tetO knock-in homozygote were analyzed. Mlc1 protein is not detectable in Mlc1 STOP-tetO knock-in homozygote. Samples from two mice per genotype are shown. (B) The level of Mlc1 protein in tetO knock in homozygotes was 97% compared with those of wild type. The extract levels were normalized by β-actin content. (C) Western blot data with NL3 antibody show the same protein sizes from wild type (+/Y), Neuroligin 3 tetO knock-in (tetO/Y), Mlc1-tTA::Neuroligin 3 tetO knock-in mice, and Neuroligin 3 STOP-tetO knock-in (STOP-tetO/Y), suggesting normal splicing. Total brain protein extracts were analyzed. Samples from two mice per genotype are shown. (D) The level of NL3 protein in tetO knock in mouse was 106% compared with those of wild type. The extract levels were normalized by tubulin content. Error bars indicate SEM.

Figure 1:
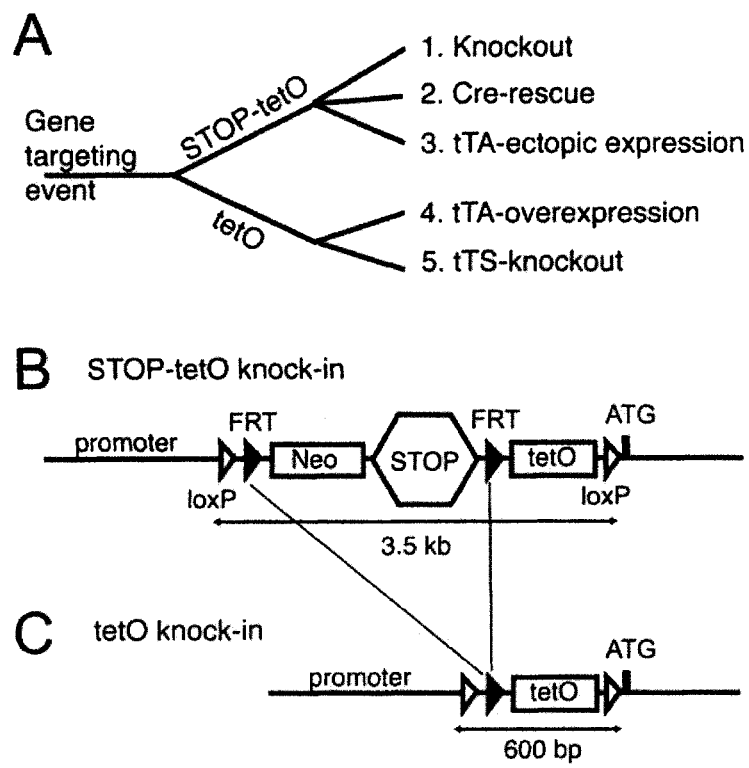
FIG. 1(A-C). FAST system. (A) Diagram of diverse applications of FAST system. A single gene targeting event yields two distinct knock-in mice (STOP-tetO and tetO), which ultimately yield 5 different applications. (B) Strategy for insertion of STOP-tetO cassette into Mlc1 locus (Mlc1 STOP-tetO knock-in mouse). Open triangles represent loxP sites. Filled triangles represent FRT sites. Neo is the PGK-EM7-NEO minigene and is in the sense orientation. STOP is the cassette containing elements designed to terminate both transcription and translation. ATG represents the translation initiation site. tetO is the cassette containing the tetracycline operator site and CMV minimal promoter. The STOP-tetO cassette (3.5 kb) was inserted just upstream to ATG. (C) Mlc1 tetO knock in mouse. The Neo-STOP minigene was removed by crossing with ROSA-Flpe mice, yielding flippase-FRT recombination. The tetO sequence (600 bp) remained upstream to ATG.

Ctx, cortex; St, striatum; Gpi, globus pallidus interna; SN, substantia nigra.

DETAILED DESCRIPTION OF THE INVENTION

Definitions

As used in this application, except as otherwise expressly provided herein, each of the following terms shall have the meaning set forth below.

"Knockout" shall mean suppression of a gene expression at a locus such that transcription of gene is undetectable using standard laboratory techniques.

"Conditional knockout/knockdown" shall mean suppression of a gene in a given tissue.

"Cre" shall mean Cre recombinase.

"Cre-mediated rescue" shall mean expression of a gene from a locus previously inserted with the STOP-tetO cassette.

"Overexpression" shall mean expression of a gene above endogenous levels.

"DOX" shall mean doxycycline.

Exemplary Embodiments of the Invention

This disclosure provides a targeting vector for in vivo gene regulation in a eukaryotic cell, wherein the targeting vector introduces the LoxP-FRT-Neo STOP-FRT-tetO-LoxP cassette at a particular locus in the genome.

In one embodiment, the locus is at or near gene X. In one another embodiment gene X is any gene expressed in a eukaryotic cell.

In one embodiment, the eukaryotic cell is a mammalian cell. In another embodiment the eukaryotic cell is a plant cell.

In one embodiment, the vector comprises in a 5' to 3' direction when inserted into a eukaryotic genome:
(A) a first DNA sequence comprising a promoter of gene X;
(B) a second DNA sequence comprising a cis-acting target recognized by a recombinase;
(C) a third DNA sequence comprising a cis-acting target recognized by a recombinase;
(D) a positive selectable marker;
(E) a negative selectable marker;
(F) a fourth DNA sequence consisting of a STOP sequence
(G) a fifth DNA sequence comprising a cis-acting target recognized by a recombinase;
(H) a sixth DNA sequence comprising a cis-acting target for a transcriptional activator and a transcriptional repressor;
(I) a seventh DNA sequence comprising a cis-acting target recognized by a recombinase;
(J) an eighth DNA sequence comprising the translation initiation of gene X In one embodiment, the said second and seventh DNA sequence comprising a cis-acting target is recognized by a recombinase. In another embodiment the recombinase is Cre.

In one embodiment, the said third and fifth DNA sequence comprising a cis-acting target is recognized by a recombinase. In another embodiment the recombinase is Flippase.

In one embodiment, the positive selectable marker is NEO.

In one embodiment, the negative selectable marker is HSV tk.

In one embodiment, the said sixth DNA sequence comprises a cis-acting target for a transcriptional activator and a transcriptional repressor comprises tetO sequences. In another embodiment the transcriptional activator is tTA. In yet another embodiment the transcriptional repressor is tTS.

In one embodiment, the said second and seventh DNA sequence comprising a cis-acting target is LoxP.

In one embodiment, the third and fifth DNA sequence comprising a cis-acting target is FRT.

In one embodiment, the STOP sequence is a transcriptional terminator. In another embodiment the STOP sequence terminates transcription originating from said first DNA sequence.

In one embodiment, cre recombinase removes DNA sequence between said second and seventh DNA sequence thereby allowing transcription of gene X from said first DNA sequence.

In one embodiment, binding of tTA to TetO allows transcription of gene X.

In one embodiment, Flippase removes DNA sequence between said third and fifth DNA sequence.

In one embodiment, binding of tTA to TetO overexpresses the gene X.

In one embodiment, tTA is inhibited using DOX thereby allowing endogenous levels of transcription of gene X.

In one embodiment, binding of tTS to tetO suppresses transcription of gene X.

In one embodiment, tTS is inhibited using DOX thereby allowing endogenous levels of transcription of gene X.

This disclosure provides a method of generating transgenic mice having integrated in its genome LoxP-FRT-Neo STOP-FRT-tetO-LoxP cassette at a particular locus.

In one embodiment, the locus is in or near gene X.

In one embodiment, gene X is any gene expressed in the mouse. In another embodiment, gene X is Mlc1, serotonin 1A receptor, serotonin 1B receptor, or Neuroligin 3.

In one embodiment, the LoxP-FRT-Neo STOP-FRT-tetO-LoxP cassette is inserted immediately upstream of the translation initiation site of gene X.

In one embodiment, the insertion of the LoxP-FRT-Neo STOP-FRT-tetO-LoxP cassette immediately upstream of the translation initiation site of gene X generates gene X STOP-tetO mice. In another embodiment, expression of gene X is suppressed in homozygous gene X STOP-tetO mice.

In one embodiment, crossing of gene X STOP-tetO mice with mice expression Cre under the control of a specific promoter sequence results in homozygous gene X STOP-tetO::Cre mice. In another embodiment, Cre-mediated recombination in a gene X STOP-tetO::Cre mice generates expression of gene X above that detected in homozygous gene X STOP-tetO mice.

In one embodiment, crossing of gene X STOP-tetO mice with mice expression tTA under the control of a specific promoter sequence generates homozygous gene X STOP-tetO::tTA mice. In another embodiment, tTA-mediated rescue in a gene X STOP-tetO::tTA mice generates expression of gene X above that detected in homozygous gene X STOP-tetO mice.

In one embodiment, crossing of gene X STOP-tetO mice with mice expression Flippase under the control of a specific promoter sequence generates homozygous gene X STOP-tetO::Flippase mice. In another embodiment, Flippase-mediated recombination in a homozygous gene X STOP-tetO::Flippase mice generates deletion of sequences between two FRT sites thereby resulting in a gene X tetO knock-in mice.

In one embodiment, crossing of gene X tetO knock-in mice with mice expressing tTA under the control of a specific promoter sequence results in homozygous gene X tetO knock-in::tTA mice. In another embodiment, tTA-mediated rescue in a gene X tetO knock-in::tTA mice generates expression of gene X above that detected in homozygous gene X tetO knock-in mice. In yet another embodiment, administration of doxycycline to homozygous gene X tetO knock-in::tTA mice suppresses expression of gene x such that expression of gene X is detected below that detected in homozygous gene X tetO knock-in::tTA mice.

In one embodiment, crossing of gene X tetO knock-in mice with mice expressing tTS under the control of a specific promoter sequence generates homozygous gene X tetO knock-in::tTS mice. In another embodiment, tTS-mediated suppression in a gene X STOP-tetO::tTS mice generates expression of gene X below that detected in homozygous gene X tetO knock-in mice. In yet another embodiment, administration of doxycycline to homozygous gene X tetO knock-in::tTS mice enhances expression of gene x such that expression of gene X is detected above that detected in homozygous gene X tetO knock-in::tTS mice without doxycycline administration.

EXPERIMENTAL DETAILS

Experiment 1

Figure 4:
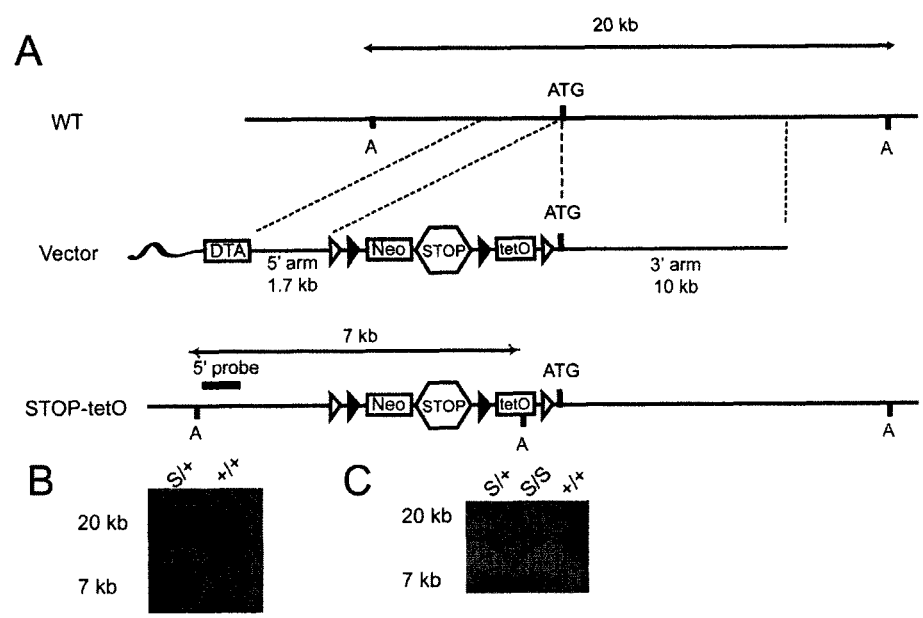
FIG. 4(A-C). Mlc1 gene targeting. (A) Diagram depicting the strategy for insertion of STOP-tetO cassette into Mlc1 locus. Using pNeoSTOPtetO plasmid and BAC recombination we obtained the targeting vector as shown in "vector". The location of the 5' probe is indicated by the thick bar. A is the Asp718 restriction enzyme site. (B) Southern blot with DNA from ES cells. The predicted sizes of Asp718 digests were 20 kb for wild type and 7 kb for the insertion mutation. (C) Southern blot with DNA extracted from F1 offspring. The same predicted sizes of the Mlc1+/+ and Mlc1 STOP/STOP alleles seen in B are obtained.

Yielding Two Distinct Mlc1 Mouse Lines: STOP-tetO and tetO Knock-in from a Single Gene Targeting Event A single gene targeting event was achieved by inserting a loxP-FRT-Neo STOP-FRT-tetO-loxP cassette immediately upstream of the translation initiation site in exon 2 of the Mlc1 gene using conventional homologous recombination, resulting in Mlc1 STOP-tetO knock-in mice (FIG. 1B and FIG. 4). By crossing Mlc1 STOP-tetO knock-in mice with Flippase expressing mice (ROSA-Flpe mice) (6), the FRT-flanked Neo STOP minigene was removed through Flippase-FRT recombination. This cross yielded Mlc1 tetO knock-in mice (FIG. 1C).

Experiment 2

Effect on Mlc1 Transcription in Mlc1 STOP-tetO Homozygous Mice

Figure 2:
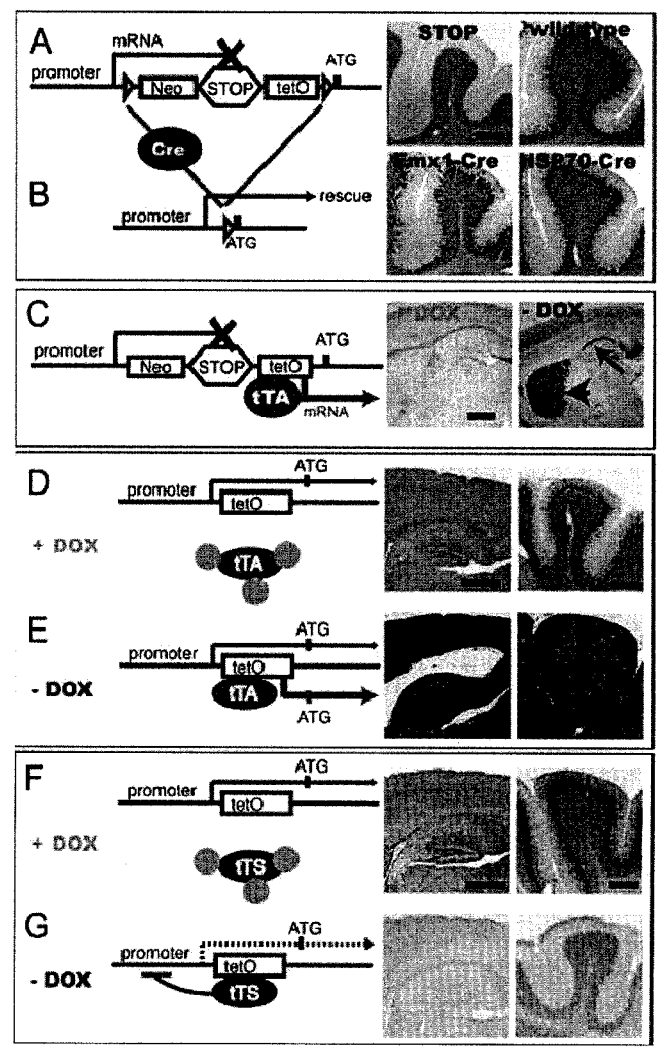
FIG. 2(A-G). Five distinct gene manipulation strategies are created from a single knock-in event. (A) STOP-tetO knock in mice are indistinguishable from straight knockout mice. The STOP cassette terminates transcription. Images show Mlc1 ISH in the cerebellar lobe of STOP-tetO homozygote and wild type mice. Note that Mlc1 mRNA is expressed in astrocyte lineage cells. Scale: 200 μm. (B) Cre-mediated rescue. Cre protein excises the loxP flanking STOP-tetO cassette, and transcription is rescued. Mlc1 ISH of Emx1-Cre::Mlc1 STOP-tetO and HSP70-Cre::Mlc1 STOP-tetO homozygotes is shown. (C) tTA-mediated ectopic expression. DOX regulates tTA protein binding to the tetO sequence and subsequent transactivation (DOX−, DOX+). Ectopic neuronal Mlc1 mRNA induction was observed in αCamKII-tTA::Mlc1 STOP-tetO homozygote. Scale: 1 mm. (D,F) tetO knock in mice are indistinguishable from wild type mice. In the presence of doxycycline, tTA and tTS cannot bind the tetO site, and the level of Mlc1 expression is the same as that seen in wild type mice. Images demonstrate Mlc1 ISH in cerebral cortex and cerebellum. Scales: 1 mm in cerebral cortex; 200 μm in cerebellum. (E) tTA-mediated overexpression. In the absence of DOX in Mlc1-mtTA::Mlc1 tetO homozygotes, tTA transactivates Mlc1 mRNA in excess of transcription driven by the endogenous promoter. (G) tTS-mediated knockout. In the absence of DOX, tTS suppresses transcription in Actin-tTS::Mlc1 tetO homozygotes.
Figure 5:
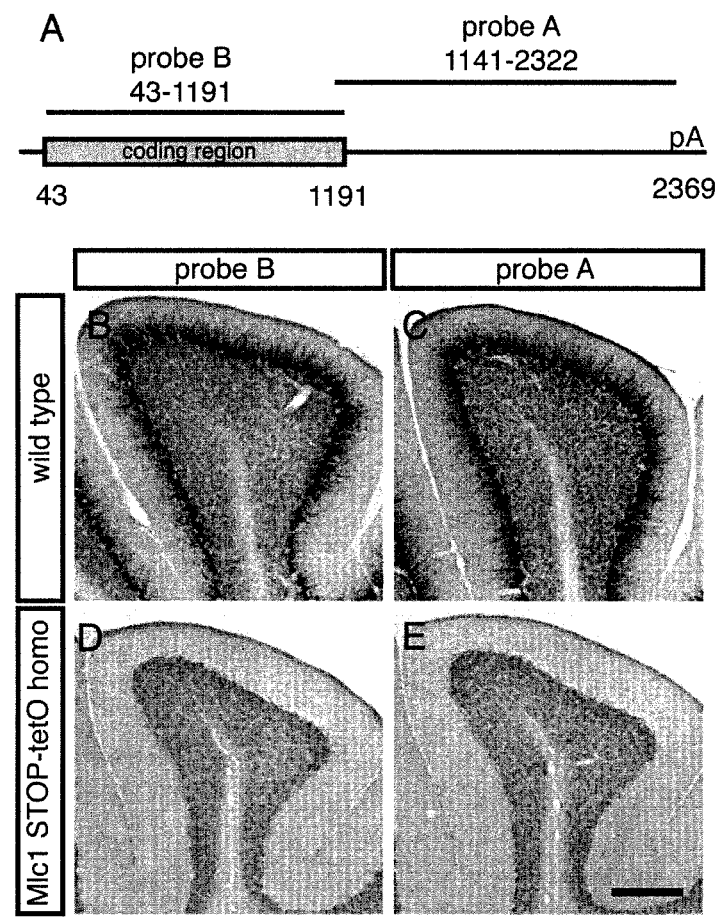
FIG. 5(A-E). Confirmation of Mlc1 gene knockout by two different cRNA probes in Mlc1 STOP-tetO knock-in homozygote. (A) Diagram depicting the region of ISH probe. Open rectangle shows the coding region of Mlc1. Left and right lines show 5'- and 3' UTR, respectively. We prepared 2 different cRNA probes; one corresponds to 3'-UTR (probe A), the other corresponds to the coding region (probe B). We used probe A in FIG. 2. (B) Mlc1 mRNA expression in wild type brain by probe A. (C) Mlc1 mRNA expression in wild type brain by probe B. (D) Mlc1 mRNA expression in Mlc1 STOP-tetO knock-in homozygote by probe A. (E) Mlc1 mRNA expression in Mlc1 STOP-tetO knock-in homozygote by probe B. Scale: 50 μm.
Figure 6:
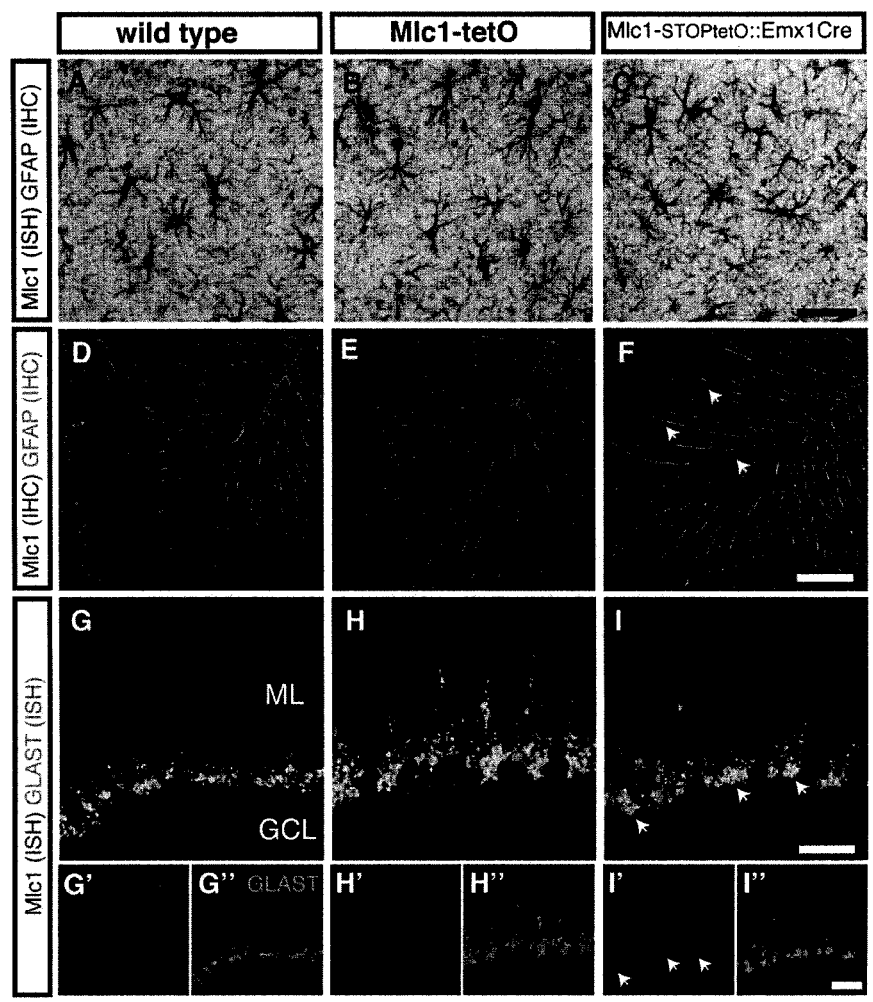
FIG. 6(A-I). Colocalization of Mlc1 with astrocytic marker in Mlc1 tetO knock-in homozygous and in Cre-mediated rescued brains. (A-C) Double labeling with Mlc1 mRNA and GFAP protein in the hippocampal CA1 region. Mlc1 mRNA and GFAP protein were visualized by NBT precipitate (blue) and DAB (brown), respectively. Mlc1 mRNA was coexpressed by GFAP positive cells in both genotypes. (D-F) Double labeling with Mlc1 protein and GFAP protein in the cerebellar Bergmann glia. Mlc1 and GFAP proteins were visualized by Alexa488 and Alexa568, respectively. Mlc1 immunoreactivity was completely overwrapped with GFAP immunoreactivity in Mlc1 tetO knock-in mice as seen in wild type mice, resulting in yellow signals. Cre-mediated rescued Mlc1 was overwrapped with GFAP (yellow color). (G-I) Double labeling with Mlc1 mRNA and GLAST mRNA in the cerebellar Bergmann glia. Mlc1 and GLAST mRNA were visualized by Cy3 and FITC, respectively. Mlc1 mRNA signals were colocalized with those of GLAST mRNA in Mlc1 tetO knock-in mice, resulting in yellow signals. Cre-mediated rescued Mlc1 mRNA signals were also colocalized.
Figure 7:
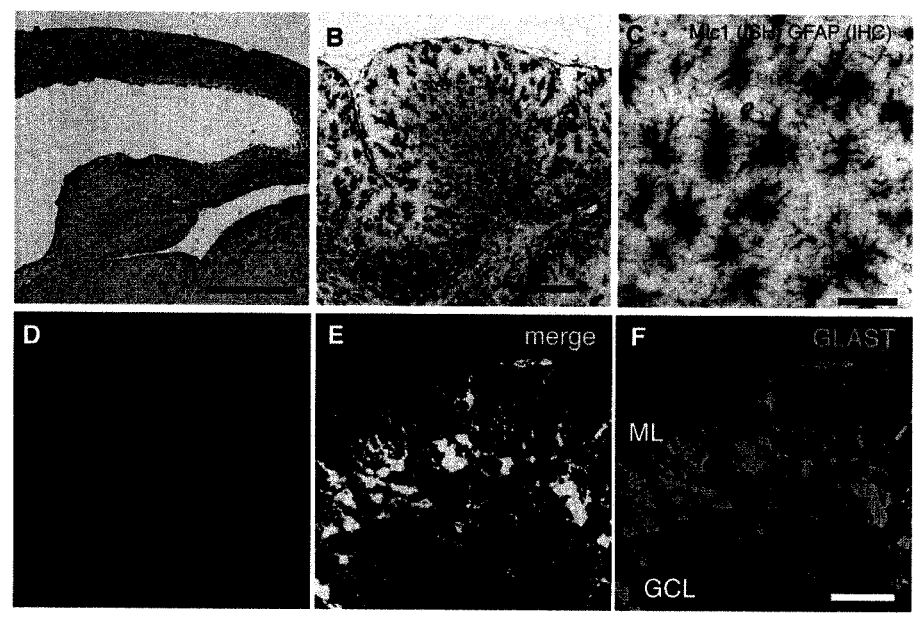
FIG. 7(A-F). Overexpression of Mlc1 mRNA in astrocytes during tTA mediated overexpression. (A, B) Mlc1 mRNA expression by lower exposure in the forebrain (A) and the cerebellum (B). Scales: 1 mm in A; 200 μm in B. (C) Mlc1 mRNA expression (NBT, blue) in GFAP positive (DAB, brown) astrocyte in the hippocampal CA1 region. Scale: 50 μm. (D-F) Mlc1 mRNA expression (Cy3 in D) in GLAST mRNA positive (FITC in F) Bergmann glia in the cerebellum. ML, molecular layer; GCL, granule cell layer; Scale: 50 μm.
Figure 8:
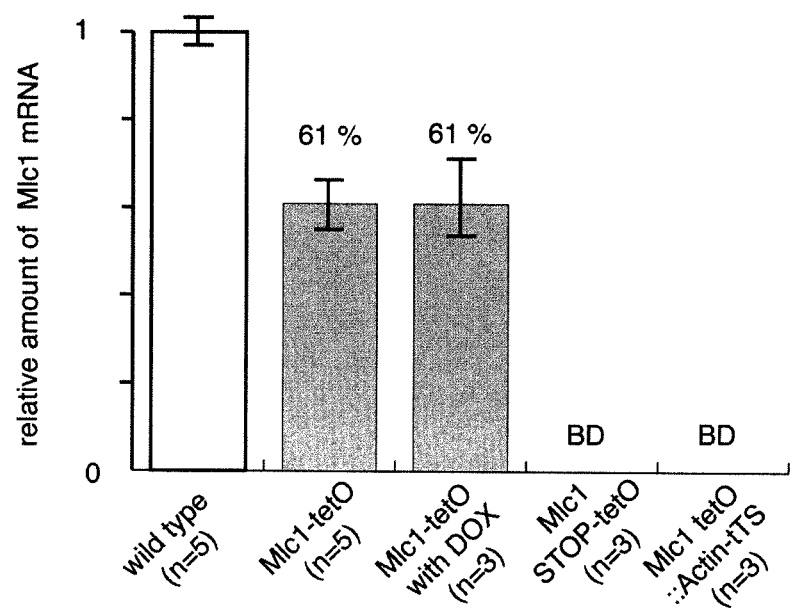
FIG. 8. Quantification of Mlc1 mRNA level. Relative amounts of Mlc1 mRNA are shown. Error bar shows standard deviation. Mlc1 tetO: Mlc1 tetO knock-in homozygote; BD: below detection.

Mlc1 expression levels were examined at postnatal day 28 in mice. In wild type mice, Mlc1 mRNA was expressed only by astrocyte-lineage cells: astrocytes, Bergmann glia and ependymal cells (FIG. 2A and FIG. 6) as detected by in situ hybridization. In Mlc1 STOP-tetO homozygous mice, Mlc1 mRNA was not detected at any age examined, since the STOP sequence terminates transcription (7) driven by the endogenous Mlc1 promoter (FIG. 2A, FIG. 5, and FIG. 8). This indicates that STOP-tetO knock-in mice act like straight null mice.

Experiment 3

Effect on Mlc1 Transcription in Mlc1 STOP-tetO Homozygous Mice Expressing Cre in Forebrain and in Germline STOP-tetO knock-in mice permit 2 further manipulations: Cre-mediated rescue (FIG. 2B) and t-TA-mediated ectopic expression (FIG. 2C). To test Cre-mediated rescue, Mlc1 STOP-tetO mice were crossed with two established Cre lines: Emx1-Cre (10) (expresses Cre mainly in forebrain) and HSP70-Cre (11) (expresses Cre in germline). Mlc1 mRNA levels were then examined in the resulting homozygous STOP-tetO::Cre mice. Emx1-Cre-mediated recombination resulted in a partial rescue as illustrated by expression in the Bergmann glia (FIG. 2B); germline Cre-mediated recombination resulted in complete rescue (FIG. 2B) (8,9).

Experiment 4

Figure 3:
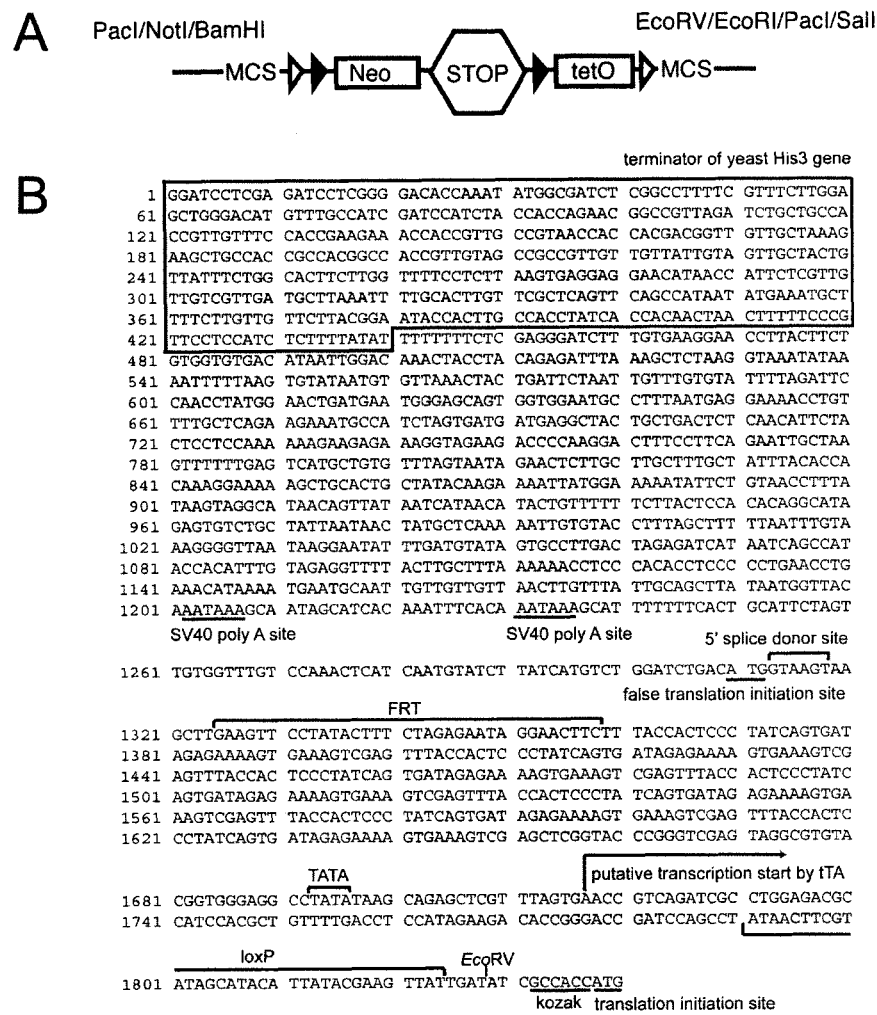
FIG. 3(A-B). pNeoSTOPtetO plasmid. (A) Construction of pNeoSTOPtetO plasmid. Open triangles represent loxP sites. Filled triangles represent FRT sites. Neo is the PGK-EM7-NEO minigene. STOP is the cassette containing elements designed to terminate both transcription and translation. ATG represents the translation initiation site. tetO is the cassette containing the tetracycline operon site and CMV minimal promoter. (B) Annotated STOP-tetO sequence (SEQ NO:1). STOP sequence consists of transcriptional terminator of yeast His3 gene (1-440, surrounded), SV40 polyadenylation sequence (441-1300), false translation initiation site (1310-1312), and 5 prime splice donor site (1313-1318). tetO sequence (1359-1790) consists of a tetracycline operator site (1359-1652) and CMV minimal promoter (1666-1790). CMV minimal promoter contains TATA box. When we made 3 prime homology arm by PCR, upper primer was designed to possess EcoRV site and kozak sequence. STOP, FRT, tetO, loxP, kozak, and translation initiation site are aligned as in the map.

Effect on Mlc1 Transcription in Mlc1 STOP-tetO Homozygous Mice Expressing tTA in Forebrain Neurons To test effect on Mlc1 transcription in Mlc1 STOP-tetO homozygous mice expressing tTA a αCamKII-tTA mice were used which express tTA in forebrain neurons. tTA protein (13) induces targeted gene transcription from a transcription initiation site within the CMV minimal promoter (FIG. 2C and FIG. 3). FIG. 2C demonstrates that tTA expression driven by the αCamKII neuronal promoter leads to ectopic Mlc1 mRNA induction in neuronal cells—e.g., hippocampal CA1 neurons (arrow) and striatum medium spiny neurons (arrowhead). Thus, by using a strain in which tTA is expression in the same region or cell type as native Mlc1 (e.g. glia), a tTA-mediated rescue experiment can be conducted (14). By using mice in which tTA is expression in a different region or cell type than the targeted gene (e.g. neurons), a tTA-mediated ectopic expression study can be conducted.

Experiment 5

Effect on Mlc1 Intron Excision and Protein Synthesis in Mlc1 STOP-tetO Homozygous Mice The 5'-UTR of mRNA transcribed under the control of tTA has a different transcription start site than endogenous mRNA (FIG. 3). To address whether this difference affects intron excision and protein synthesis in cases of genes with multiple exons such as Mlc1, the mRNA sequences and the molecular weight of proteins were examined. Total RNA from αCamKII-tTA::Mlc1-STOP-tetO homozygotes in which Mlc1 mRNA is entirely derived from tTA-mediated transcription was isolated. The Mlc1 mRNA whole open reading frame was amplified and confirmed by sequencing. All exons in the open reading frame were correctly aligned. Brain lysates were then isolated from the same mice. The size of the resulting Mlc1 protein was identical to that of endogenous protein (FIG. 9). To examine generalization of this approach, the FAST system was applied to a different multiple exon gene, Neuroligin 3 (NL3), generating NL3 STOP-tetO mice. NL3 mRNA and protein from Mlc1-mtTA (astrocyte specific tTA line, see below)::NL3 STOP-tetO homozygote brains exhibited the correct exon alignment and the same molecular weight as mRNA and protein obtained from wild type brains (FIG. 9). These experiments indicate that tTA-mediated transcription yields normal protein translation.

Experiment 6

Effect on Transcription of a Gene In Vivo by the Insertion of the tetO Sequence Upstream of that Gene's Translation Initiation Site To perform tTA-mediated overexpression and tTS-mediated conditional knockdown, 2 things are required: 1) insertion of the tetO sequence upstream of the translation initiation site, and 2) verification that tetO knock-in mice demonstrate wild type expression patterns. Since insertion of tetO, which consists of a tetracycline operator site and CMV minimal promoter (13), may change transcription efficiency, gene expression levels with or without tetO sequence insertion were compared in vitro and in vivo.

First it was verified in cell culture that insertion of tetO between various promoters and coding sequences did not significantly alter transcription. In co-transfection experiments, it was demonstrated that tetO-containing vectors could be transactivated by tTA and silenced by tTS (data not shown).

Figure 10:
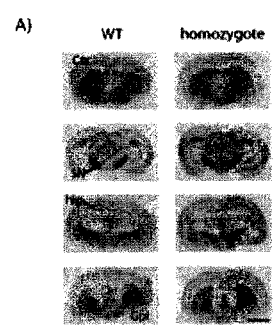
FIG. 10(A-B). (A) Htr1B expression with or without tetO insertion. Htr1B receptor autoradiogram demonstrates that tetO insertion does not have any significant effects on Htr1B receptor expression. Scale bar: 275 μm. (B) Table demonstrates the absence of ectopic expression in tetO-Htr1A and tetO-Htr1B mice. Expression of serotonin 1A and 1B receptors was seen in all expected regions as measured by autoradiography. No ectopic expression was seen when receptor expression was compared to that seen in wild type controls.

The effect of tetO insertion was examined in vivo. In addition to Mlc1 tetO and Neuroligin 3 tetO knock-in mice, 2 other tetO knock-in mice were generated: serotonin 1A receptor (Htr1A) tetO knock-in mice and serotonin 1B receptor (Htr1B) tetO knock-in mice. The tetO sequence was inserted just upstream of the translation initiation site in all cases. Levels of Mlc1 protein and NL3 protein without doxycycline (DOX) treatment by Western blot was determined. The levels of Mlc1 and NL3 proteins in tetO knock in homozygotes were 97% and 106% compared respectively with those of wild type. Levels of Htr1A and Htr1B protein without DOX treatment by quantitative receptor autoradiography was also determined. As previously reported (15), the knock-in to the Htr1A locus resulted in ~20% less binding by quantitative receptor autoradiography. (data not shown). In Htr1B tetO knock-in homozygotes, there were no significant differences in Htr1B protein levels in most brain regions, with less than 10% increases in the striatum and substantia nigra. (FIG. 10; data not shown). Taken together, the in vitro and in vivo data suggest that eh insertion of the tetO sequence is unlikely to significantly disrupt endogenous protein expression. In fact, in the four in vivo examples described here, no evidence of significant disruption was seen.

Insertion of tetO also lengthens the mRNA 5'-UTR, which could potentially affect either transcriptional or translational regulation. For example, the 5'-UTR can have effects on transcriptional efficiency, mRNA splicing events (especially in exons 1 and 2), mRNA stability, and translation efficiency. Therefore whether tetO insertion affects mRNA splicing, mRNA expression levels, and mRNA expression patterns for Mlc1 and Neuroligin 3 was examined. First the mRNA sequence of tetO knock-in mice was examined and correct mRNA splicing was confirmed (data not shown). Next molecular weights with or without tetO insertion by Western blotting were compared. In both Mlc1 and Neuroligin 3, the molecular weights of proteins from tetO knock-in mice were identical to those from wild type mice, suggesting that the lengthened mRNA did not affect splicing (FIG. 9); this is not an issue for Htr1A and Htr1B, as they do not have introns. mRNA levels by quantitative RT-PCR were then measured. In the case of the Mlc1 gene, though homozygous tetO insertion decreased mRNA levels to 61% of wild-type (FIG. 8), the expression pattern of Mlc1 mRNA was identical to wild-type (e.g. coexpressed with astrocytic markers in appropriate brain regions) (FIG. 6); no ectopic expression was seen. In addition, protein levels appear to be similar using Western blot (FIG. 9). Although mRNA levels in this case are affected, the tetO knock-in mouse still demonstrates the appropriate wild type gene expression pattern and protein levels.

Experiment 7

Effect on Mlc1 Transcription in Mlc1 tetO Knock-in Homozygous Mice Expressing tTA in Astrocytes To test tTA-mediated overexpression, astrocyte specific tTA mice were generated, crossed with Mlc1 tetO knock-in mice, and Mlc1 mRNA levels were examined. FIGS. 2D and 2E show the expression of Mlc1 mRNA in Mlc1-mtTA::Mlc1-tetO mice in the presence of doxycycline (DOX) and absence of DOX, respectively. In the presence of DOX, tTA cannot bind the tetO sequence, preventing additional transactivation of Mlc1 (FIG. 2D). In the absence of DOX, tTA binds tetO and initiates transcription in excess of endogenous transcription, resulting in Mlc1 overexpression in astrocytes (FIG. 2E and supplementary fig S5).

Experiment 8

Effect on Mlc1 Transcription in Mlc1 tetO Knock-in Homozygous Mice Expressing tTS Under an Actin Promoter To validate conditional knockout/knockdown, a tTS system was used. tTS is a tetracycline-dependent transcriptional-silencer containing the Kruppel-associated box (KRAB) domain of human zinc finger protein 10 (16). KRAB works as a transcriptional silencer extending over regions of a radius of 3 kilobases when tethered to DNA. The binding of ITS protein to DNA is also reversibly controlled by DOX (FIGS. 2F and 2G). In Actin-tTS::Mlc1-tetO homozygous mice, tTS protein was expressed ubiquitously under the control of human β-actin promoter. In the absence of DOX, tTS binds tetO sites and the Mlc1 promoter is widely suppressed; mRNA and protein were not detectable by in situ (FIG. 2G), RT-PCR (FIG. 8), or Western blotting (FIG. 9). Thus Actin-TS::Mlc1-tetO mice without DOX function as knockout mice. In the presence of DOX, tTS cannot bind tetO sites and the Mlc1 promoter drives transcription, resulting in wild type Mlc1 expression (FIG. 2F). In the case of the serotonin 1A receptor, the tTS system can be used to produce tissue-specific knockouts/knockdowns by using mice that express tTS selectively in the raphe nuclei or in the hippocampus (Richardson-Jones et al, in press). In addition these tissue-specific knockouts/knockdowns can be inducible (only in adulthood for example) and reversible (Richardson-Jones et al, in press).

Discussion

Using a new technological approach, a problem of increasing the speed of the screening process of mice was circumvented by generating several different mouse strains from one single gene-targeting event. This system—FAST (Flexible Accelerated STOP TetO-knockin)—includes the single gene targeting event and five versatile applications (FIG. 1A). It allows us to take advantage of established Cre-recombinase, tTA (tetracycline-controlled transcriptional-activator), and tTS (tetracycline-controlled transcriptional-silencer) lines to rapidly produce 5 separate lines of mice from the original knock-in: 1) knockout; 2) Cre-mediated rescue; 3) tTA-mediated ectopic expression; 4) tTA-mediated overexpression; and 5) tTS-mediated conditional knockout/knockdown. Applications #4 and #5 require breeding with FLPe mice to remove the stop sequence and obtain the second knock-in. This flexibility allows one to efficiently develop many different disease models by altering expression of a single gene.

The FAST system described here demonstrates versatile manipulation of gene expression. While the gene targeting methods used are similar to those used in classical systems, both requiring ES cell homologous recombination and germline transmission, our system utilizes existing methods of gene manipulation in as efficient and flexible a way as possible. This approach allows optimized screening of mice with variable gene expression patterns, in the hopes of more efficiently finding useful disease models. It is demonstrated that a single gene targeting event yields two distinct knock-in mice, ultimately resulting in at least 5 different types of gene manipulations.

Applications requiring tTA or Cre mice can take advantage of diverse mouse lines already available as common sources. This versatility will serve as a template for a systematic approach to performing in vivo gain and loss of function studies. The tetO sequence is a key element of this system, as it is bound by tTA and tTS proteins, and thus permits multiple types of gene manipulation to be conducted. Using four different tetO knock-in mice, the robustness of this system has have demonstrated: 1) tetO insertion does not affect overall protein expression levels, which was not necessarily expected, and 2) the change in 5'-UTR due to tetO insertion does not affect mRNA splicing, as demonstrated both by Western blot and DNA sequencing; in addition, the insertion does not affect the mRNA expression pattern.

These five different applications allow a variety of different studies of gene expression to be performed. For example, unlike the Cre-loxP system, which causes an irreversible knockout, the tTS system allows reversible gene knockout; this is useful not only in developmental studies, but also in temporary gene knockout/knockdown and recovery experiments, mimicking disease conditions and recovery with or without treatments. In tTS-mediated systems, the degree of gene knockdown can theoretically be controlled by the dosage of doxycycline. Mice with different levels of expression could potentially mimic different states of epigenetic gene expression, which may be linked to phenotypes in particular developmental disorders. An additional advantage of the tTS system over knockout strategies employing inducible recombinases (such as Cre-ER) is that the level of knockout achieved seems to be superior; this is based on the fact that between 90-100% recombination using the tTS system has been seen (Richardson-Jones et al in press (20); and unpublished data), versus at most 50% recombination efficiency with the CreER-loxP system (specifically using Nestin-CreER, Olig2-CreER, and GFAP-CreER mice with loxP-reporter mice). In the four loci studied a full knockout has been obtained, while the Cre-ER system usually achieves only a partial knockout. In addition, the results with the FAST system indicate that the tetO knockin yields superior tTA transactivation efficiency when compared to classic transgenic systems using tetO-cDNAs.

The FAST system offers distinct advantages over other transgenic approaches for studying human genetic diseases or gene expression in general. The rapid production of both tissue-specific and inducible knockout mice and overexpressing mice for an individual gene enables one to readily address which expression patterns may contribute to specific phenotypes. Such tools should accelerate the ability to dissect the circuits and mechanisms underlying various neuropsychiatric diseases, increase the pace of screening of novel drugs, and ultimately lead to the production of new treatments.

Despite its many advantages over traditional approaches, the FAST system has several limitations. First, tTS mice are not yet widely available, which limits the current utility of application #5 (though it is expected that these lines will be more widely available in the near future). In addition, the FAST system would probably not be useful for genes with multiple promoters and translation initiation sites. Another consideration is a problem that is applicable to all systems using tetracycline-regulatable gene expression, and not specific to the FAST system: tTA and tTS may bind pseudo tetO sequences in the mouse genome, thus disturbing the general transcriptional network. Similarly, as with other applications using tTA or tTS, the VP16 activator domain in tTA may bind the sites with similarity to TBP, TFIIB, or TAF40 (18); and the KRAB silencer domain in tTS may bind the sites with similarity to KAP-1 (19). Finally, as with all systems using tetracycline-regulatable gene expression, one must be aware of potential side effects of doxycycline, and the possibility that diurnal variation of doxycycline levels may affect expression of a target gene.

In future studies, the location of the tetO sequence could be an important factor in cases of tTS-mediated gene knockout. The KRAB silencer domain, a tTS component, represses over regions of 2-3 kilobases. If the length between the transcription and translation initiation sites is greater than 3 kB, tTS-mediated gene knock down would be difficult. In our case, the lengths are 0.5 kB (Mlc1) and 2.8 kB (NL3), and tTS-mediated gene knockout/knockdown was successful (FIG. 2G; data not shown).

The FAST system allows one to significantly accelerate this process by rapidly generating multiple lines of mice that provide a spectrum of expression levels for single genes, from selective knockout to selective overexpression. In addition, the FAST system has the added advantage of easily integrating temporal and spatial specificity into the manipulations of gene expression. Here it is demonstrated the efficacy of the FAST system using multiple genes implicated in neuropsychiatric disorders. One of the overall goals is to use the FAST system to make mouse models using genes that have been linked to disease, but 1) have unknown function and 2) have not yet been knocked out in mice. Therefore the Mlc1 gene was chosen to start the initial test of the system, since its function is unknown (though homology to other proteins suggests that it may be an integral membrane transporter (3)), and knockout mice have not yet been made. Mutations in this gene have been associated with megalencephalic leukoencephalopathy with subcortical cysts, an autosomal recessive neurological disorder (3); Mlc1 has also been implicated in catatonic schizophrenia (4). It is describe here that gene targeting in detail as proof of principle of efficacy of the FAST system. Moreover, it is demonstrated the broad applicability of the FAST system by targeting three additional genes of importance in neuropsychiatric disorders: the serotonin 1A receptor (depression, anxiety); the serotonin 1B receptor (addiction, impulsive aggression, OCD); and Neuroligin 3 (autism) (5).

Methods

Generation of Gene Targeting Vector:

A pNeoSTOPtetO plasmid (FIG. 3A) was manufactured in which the following elements were connected in tandem: multicloning site1 (PacI/NotI/BamHI), loxP, FRT, PGK-EM7-Neo-HSV thymidine kinase poly A minigene, STOP sequence, FRT, tetO sequence, loxP, multicloning site2 (EcoRV/EcoRI/PacI/SalI). 400 bp of DNA fragments both upstream and downstream of the translation initiation site were amplified with PCR primers containing appropriate restriction enzyme sites, and respectively inserted into each multicloning site of the pNeoSTOPtetO plasmid. In order to perform BAC recombination, the NeoSTOPtetO cassette with 400 bp homology arms was transferred into the bacteria carrying the BAC and the pBADTcTypeG plasmid. The targeting vector was isolated from the recombined, kanamycin resistant clone by using a retrieving technique into pMCS-DTA plasmid. Subsequently, a targeting vector was obtained comprised of 10 kb 3-prime homology arm, NeoSTOPtetO cassette, 1.7 kb 5-prime homology arm, and diphtheria toxin A subunit (DTA).

Southern Blotting:

Genomic DNA with Asp718 was digested, fragments were separated through a 0.8% agarose gel, and blotted on a nylon membrane. $^{32}$P-random-prime-labeled probe was hybridized. Probe position was from −3457 to −2899 bases upstream to the translation initiation site and was located outside the region of homology arm. Predicted sizes were 20 kb in the wild type allele and 7 kb in the Mlc1-STOP-tetO allele.

Generation of STOP-tetO and tetO Knock-in Mice:

The targeting vector was designed to insert the STOP-tetO cassette just upstream of the Mlc1 gene translation initiation site. 129 SvEv ES cells (line CSL3) were used (FIGS. 3 and 4). Four recombined clones were obtained out of eighty G418 resistant clones. Germline transmitted offspring were established as Mlc1 STOP-tetO heterozygous knock-in mice (FIG. 3B). Mlc1 STOP-tetO mice were crossed with ROSA-Flpe mice, and FRT flanking NeoSTOP sequences were removed (FIG. 1C). Mlc1 tetO knock in mice were subsequently generated. Similar methods were used for Neuroligin 3, Htr1A, and Htr1B genes. Mlc1-mtTA BAC transgenic mice (see below), αCamKII-tTA mice, Emx1-Cre mice, HSP70-Cre mice, and Actin-tTS mice were used for studies of manipulation of gene expression.

Doxycycline Treatment:

Doxycycline was administered by feeding with 100 mg/kg doxycycline containing chow. All animal procedures were conducted in accordance with the guidelines described by the National Institutes of Health Guide for the Care and Use of Laboratory Animals, and the Institutional Animal Care and Use Committee of Columbia University and National Institute for Physiological Sciences (Japan).

Generation of Mlc1-mtTA Mice:

The codons of bacterial tetracycline repressor protein and viral VP16 activator domain were fully mammalianized. Mouse BAC DNA (clone RP23-114I6) was initially modified by inserting Rps1-Zeo cassette into the translation initiation site of Mlc1 gene followed by the replacement with a cassette containing mtTA and SV40 polyadenylation signal. BAC DNA was linearized by PI-SceI enzyme digestion, and injected into fertilized eggs from CBA/C57BL6 mice.

Mouse Genotyping:

The following PCR primer sets were used in mouse genotyping: MlcU-657 (5'-AAATTCAGGAAGCTGTGTGC-CTGC-3') (SEQ ID NO:2) and mtTAL24 (5'-cggagttgatcac-cttggacttgt-3') (SEQ ID NO:3) for Mlc1-mtTA mice; NNU (5'-aggcttgagatctggccatac-3') (SEQ ID NO:4) and XZTL (5'-aagggcaaaagtgagtatggtg-3') (SEQ ID NO:5) for αCamKII-tTA mice; CreP1 (5'-GCCTGCATTACCGGTCGATG-CAACG-3') (SEQ ID NO:6) and CreP2 (5'-AAATCCATCGCTCGACCAGTTTAGTTACCC-3') (SEQ ID NO:7) for Emx1-Cre and HSP70-Cre mice; ttsP1 (5'-ttgatcaccaaggtgcagag-3') (SEQ ID NO:8) and ttsP2 (5'-cagggctcttctcccttctc-3') (SEQ ID NO:9) for Actin-tTS mice. The sizes of PCR product are approximately 680 bp, 300 bp, 600 bp and 400 bp, respectively, and wild type mice are negative for the above sets. The primer set with Mlc-80U (5'-AGGGAATGGTGGTCTGAGTCTGTT-3') (SEQ ID NO:10) and Mlc159L (5'-GAGAACACCCATGTCTTG-TAGCTG-3') (SEQ ID NO:11) yields a 240 bp band from the wild type allele, 850 bp band from the Mlc1 tetO knock in allele, and no band from the Mlc1 STOP-tetO knock in allele. The MlcU-657 and PGKproL1 set (5'-GTTGGcgcctaccggtg-gatgtggaatgtg-3') (SEQ ID NO:12) yields an 800 bp band from the Mlc1 STOP-tetO knock in allele, and no band from wild type and Mlc1 tetO knock in alleles.

Western Blotting:

Mouse brains were homogenized in 10% (tissue weight/buffer volume) lysis buffer [100 mm NaCl, 50 mM Tris, pH 8.0, 1% (w/v) Triton X-100, 0.1% (w/v) sodium dodecylsulphate, 2 mm dithiothreitol, complete protease inhibitor cocktail; protein concentration was measured with a bicinchoninic acid protein assay. For NL3 blots, homogenized tissue was prepared in 4× Laemmli buffer. For Mlc1 blots, homogenates were incubated on ice for 20 min and then centrifuged at 3000×g for 10 min at 4° C. Supernatants were centrifuged at 10,000×g for 12 min at 4° C. subsequently supernatants were ultracentrifuged at 100,000×g for 1 h at 4° C. Pellets were resuspended in SDS-sample buffer (62.5 mM Tris, pH 6.8, 2% SDS). Thirty micrograms of protein were loaded in each lane. Primary antibodies used were: rabbit anti-Mlc1 (AT-LAS, Sweden), rabbit anti-NL3, mouse anti-β-actin (clone AC-15, Sigma), mouse anti tubulin. Mlc1 blots detected with chemiluminescence were determined by densitometric quantification using ImageJ software (version 1.37, National Institutes of Health, Bethesda, Md.), and normalized by β-actin contents in the same sample (n≥3 mice per genotype). NL3 blots detected with fluorescent secondary antibodies were quantified using Odyssey System (LI COR Inc., Lincoln, Nebr.) and normalized by tubulin contents in the same sample (n≥3 mice per genotype).

In Situ Hybridization (ISH):

Cryosections from 4% paraformaldehyde perfused brains were used. Detailed methods for in situ hybridization are described elsewhere (7). In brief, digoxigenin-labeled Mlc1 cRNA probes (8) were hybridized to sections, NBT/BCIP compounds (Roche) were used for color development, and nuclear fast red (Vector Lab, Burlingame, Calif.) was used for counter-staining. The region of Mlc1 used for the cRNA probe is nt 1114-2322, corresponding to NM_133241 (2369 bp; coding region is 43-1191 bp).

Co-Labeling of Mlc1 Signal with Astrocyte Marker:

The following combinations were used: 1) Mlc1 ISH and GFAP immunohistochemistry (IHC), 2) Mlc1 IHC and GFAP IHC, and 3) Mlc1 ISH and GLAST ISH. For Mlc ISH and GFAP IHC, Mlc1 mRNA was visualized with NBT and GFAP protein was labeled with anti-GFAP antibody (mouse monoclonal antibody, GA5, Sigma). Following the incubation of biotin-tagged secondary antibody, VECTASTAIN Elite Kit (Vector Lab) was used for the color development with DAB. For double fluorescent IHC, sections were incubated with rabbit anti-Mlc1 and mouse anti-GFAP antibodies followed by the incubation of Alexa 568 (Mlc1) and Alexa 488 (GFAP) tagged antibodies (Invitrogen, USA). For double fluorescent ISH, digoxigenin-labeled Mlc1 cRNA and FITC-labeled GLAST cRNA probes were hybridized to sections. Mlc1 and GLAST probes were visualized with Cy3 and FITC, respectively, using TSA-Plus system (PerkinElmer, USA).

Quantitative RT-PCR:

Total RNA was isolated from cerebellum. cDNA was synthesized using random hexamer and Superscript II reverse transcriptase (Invitrogen, Carlsbad, Calif.). The level of Mlc1 mRNA was determined using commercial primers and a Taq-Man probe (assay ID: Mm00453827_m1, Applied Biosystems, Foster City, Calif.); levels were normalized using beta-actin mRNA content.

Receptor Autoradiography:

Cryosections from fresh frozen brains were used. For 5-HT1A binding, coronal sections (18 μm) were preincubated in binding buffer (50 mM Tris-HCl, pH 7.4, 2 mM MgCl2) for 30 min, before incubation in binding buffer containing 0.14 nM $^{125}$I-MPPI (Htr1a ligand, kindly provided by Karl Ploessl and Hank Kung, Department of Radiology, University of Pennsylvania, Pa.). For 5-HT1B binding, sections were preincubated for 1 hour in binding buffer (50 mM Tris-HCl, pH 7.4, 0.01% ascorbic acid, 10 μM pargyline, 3 μM isoproterenol, 100 nM 8-OH-DPAT, 0.3% BSA), followed by 2 hr incubation in binding buffer containing 0.14 nM $^{125}$I-CYP (Htr1b ligand, Perkin Elmer, Waltham, Mass.). Sections were then washed in ice cold binding buffer (two times for 10 min), rinsed in distilled water and air-dried. Slides were exposed to single-sided Kodak BioMax film for 2-4 days. The relative abundance of ligand binding sites was determined by measuring mean luminosity of autoradiograms using Adobe Photoshop software, and comparing these values to those generated from a $^{125}$I standard. Mean luminosity from 6-10 sections per brain region per animal were averaged and expressed as total microcuries using the standard curve.

Doxycycline Treatment:

Doxycycline (Sigma) was administered by feeding with 100 mg/kg doxycycline containing chow (Nosan Co, Japan). All animal procedures were conducted in accordance with the guidelines described by the National Institutes of Health Guide for the Care and Use of Laboratory Animals, and the Institutional Animal Care and Use Committee of Columbia University and National Institute for Physiological Sciences (Japan).

REFERENCES

1. Lira A, Zhou M, Castanon N, Ansorge M S, Gordon J A, Francis J H, et al (2003): Altered depression-related behaviors and functional changes in the dorsal raphe nucleus of serotonin transporter-deficient mice. Biol Psychiatry 54:960-971.
2. Jennings K A, Loder M K, Sheward W J, Pei Q, Deacon R M, Benson M A, et al (2006): Increased expression of the 5-HT transporter confers a low-anxiety phenotype linked to decreased 5-HT transmission. J Neurosci 26:8955-8964.
3. Leegwater P A, Yuan B Q, van der Steen J, Mulders J, Konst A A, Boor P K, et al (2001): Mutations of MLC1 (KIAA0027), encoding a putative membrane protein, cause megalencephalic leukoencephalopathy with subcortical cysts. Am J Hum Genet 68:831-838.
4. Meyer J, Huberth A, Ortega G, Syagailo Y V, Jatzke S, Mossner R, et al (2001): A missense mutation in a novel gene encoding a putative cation channel is associated with catatonic schizophrenia in a large pedigree. Mol Psychiatry 6:302-306.
5. Jamain S, Quach H, Betancur C, Rastam M, Colineaux C, Gillberg I C, et al (2003): Mutations of the X-linked genes encoding neuroligins NLGN3 and NLGN4 are associated with autism. Nat Genet 34:27-29.
6. Farley F W, Soriano P, Steffen L S, Dymecki S M (2000): Widespread recombinase expression using FLPeR (flipper) mice. Genesis 28:106-110.
7. Lakso M, Sauer B, Mosinger B, Jr., Lee E J, Manning R W, Yu S H, et al (1992): Targeted oncogene activation by site-specific recombination in transgenic mice. Proc Natl Acad Sci USA 89:6232-6236.
8. Weisstaub N V, Zhou M, Lira A, Lambe E, Gonzalez-Maeso J, Hornung J P, et al (2006): Cortical 5-HT2A receptor signaling modulates anxiety-like behaviors in mice. Science 313:536-540.
9. Guy J, Gan J, Selfridge J, Cobb S, Bird A (2007): Reversal of neurological defects in a mouse model of Rett syndrome. Science 315:1143-1147.
10. Iwasato T, Datwani A, Wolf A M, Nishiyama H, Taguchi Y, Tonegawa S, et al (2000): Cortex-restricted disruption of NMDAR1 impairs neuronal patterns in the barrel cortex. Nature 406:726-731.
11. Dietrich P, Dragatsis I, Xuan S, Zeitlin S, Efstratiadis A (2000): Conditional mutagenesis in mice with heat shock promoter-driven cre transgenes. Mamm Genome 11:196-205.
12. Mayford M, Bach M E, Huang Y Y, Wang L, Hawkins R D, Kandel E R (1996): Control of memory formation through regulated expression of a CaMKII transgene. Science 274:1678-1683.
13. Gossen M, Bujard H (1992): Tight control of gene expression in mammalian cells by tetracycline-responsive promoters. Proc Natl Acad Sci USA 89:5547-5551.
14. Gross C, Zhuang X, Stark K, Ramboz S, Oosting R, Kirby L, et al (2002): Serotonin1A receptor acts during development to establish normal anxiety-like behaviour in the adult. Nature 416:396-400.
15. Audero E, Coppi E, Mlinar B, Rossetti T, Caprioli A, Banchaabouchi M A, et al (2008): Sporadic autonomic dysregulation and death associated with excessive serotonin autoinhibition. Science 321:130-133.
16. Deuschle U, Meyer W K, Thiesen H J (1995): Tetracycline-reversible silencing of eukaryotic promoters. Mol Cell Biol 15:1907-1914.
17. Mallo M, Kanzler B, Ohnemus S (2003): Reversible gene inactivation in the mouse. Genomics 81:356-360.
18. Friedman J R, Fredericks W J, Jensen D E, Speicher D W, Huang X P, Neilson E G, Rauscher F J 3rd. (1996): KAP-1, a novel corepressor for the highly conserved KRAB repression domain. Genes Dev 10:2067-2078.
19. Hall D B, Struhl K (2002): The VP16 activation domain interacts with multiple transcriptional components as determined by protein-protein cross-linking in vivo. J Biol Chem 277:46043-46050.
20. Richardson-Jones, J W, Hen R, Leonardo E. D. et al. (in press): 5-HT1A autoreceptor levels determine vulnerability to stress and response to antidepressants. Neuron.

What is claimed is:

1. A targeting vector for in vivo gene regulation in a murine cell, wherein the targeting vector introduces the LoxP-FRT-Neo STOP-FRT-tetO-LoxP cassette at, near, or in gene X in the murine genome.

2. The vector of claim 1 comprising in a 5' to 3' direction when inserted into a murine genome the following elements:
   A) a first DNA sequence comprising a promoter of gene X;
   B) a second DNA sequence comprising a cis-acting target, that is recognized by a recombinase;
   C) a third DNA sequence comprising a cis-acting target, that is recognized by a recombinase;
   D) a positive selectable marker;
   E) a negative selectable marker;
   F) a fourth DNA sequence consisting of a STOP sequence;
   G) a fifth DNA sequence comprising a cis-acting target, that is recognized by a recombinase;
   H) a sixth DNA sequence comprising a cis-acting target for a transcriptional activator and a transcriptional repressor;
   I) a seventh DNA sequence comprising a cis-acting target recognized by a recombinase; and
   J) an eighth DNA sequence comprising the translation initiation site of gene X.

3. The vector of claim 2, wherein the negative selectable marker in element E) is HSV tk.

4. The vector of claim 2, wherein the sixth DNA sequence in element H) comprises a cis-acting target for a transcriptional activator and a transcriptional repressor comprises tetO sequences.

5. A method of transcribing gene X from the vector of claim 2, comprising contacting the second DNA sequence and the seventh DNA sequence with Cre recombinase, wherein the Cre recombinase removes any DNA sequence between the second DNA sequence and the seventh DNA sequence, thereby allowing transcription of gene X from the first DNA sequence comprising a promoter of gene X.

6. A method of transcribing gene X from the vector of claim 2, comprising contacting tTA with the sixth DNA sequence, wherein the cis-acting target of a transcriptional activator is TetO and the binding of tTA to TetO allows transcription of gene X.

7. The method of claim 6, wherein binding of tTA to TetO overexpresses the gene X.

8. The method of claim 7, wherein tTA is inhibited using DOX thereby allowing endogenous levels of transcription of gene X.

9. A method of transcribing gene X from the vector of claim 2, comprising contacting tTS with the sixth DNA sequence, wherein the cis-acting target of a transcriptional repressor is TetO and wherein the binding of tTS to tetO suppresses transcription of gene X.

10. The method of claim 9, wherein tTS is inhibited using DOX thereby allowing endogenous levels of transcription of gene X.

11. A population of cells transfected with the vector of claim 1.

12. A method of generating a transgenic mice comprising integrating into a mouse a LoxP-FRT-Neo STOP-FRT-tetO-LoxP cassette at, near, or in gene X in the murine genome.

* * * * *

SEQUENCE LISTING

```
<160> NUMBER OF SEQ ID NOS: 12

<210> SEQ ID NO 1
<211> LENGTH: 1840
<212> TYPE: DNA
<213> ORGANISM: Artificial Sequence
<220> FEATURE:
<223> OTHER INFORMATION: STOP-tetO sequence

<400> SEQUENCE: 1
ggatcctcga gatcctcggg gacaccaaat atggcgatct cggccttttc gtttcttgga      60
gctgggacat gtttgccatc gatccatcta ccaccagaac ggccgttaga tctgctgcca     120
ccgttgtttc caccgaagaa accaccgttg ccgtaaccac cacgacggtt gttgctaaag     180
aagctgccac cgccacggcc accgttgtag ccgccgttgt tgttattgta gttgctactg     240
ttatttctgg cacttcttgg ttttcctctt aagtgaggag gaacataacc attctcgttg     300
ttgtcgttga tgcttaaatt ttgcacttgt tcgctcagtt cagccataat atgaaatgct     360
```

```
tttcttgttg ttcttacgga ataccacttg ccacctatca ccacaactaa cttttccccg      420
ttcctccatc tctttatat tttttttctc gagggatctt tgtgaaggaa ccttacttct        480
gtggtgtgac ataattggac aaactaccta cagagattta aagctctaag gtaaatataa      540 aattttaag tgtataatgt gttaaactac tgattctaat tgtttgtgta ttttagattc        600
caacctatgg aactgatgaa tgggagcagt ggtggaatgc ctttaatgag gaaaacctgt     660
tttgctcaga agaaatgcca tctagtgatg atgaggctac tgctgactct caacattcta    720
ctcctccaaa aaagaagaga aaggtagaag accccaagga cttccttca gaattgctaa      780 gtttttgag tcatgctgtg tttagtaata gaactcttgc ttgctttgct atttacacca      840
caaaggaaaa agctgcactg ctatacaaga aaattatgga aaaatattct gtaacccttta   900 taagtaggca taacagttat aatcataaca tactgttttt tcttactcca cacaggcata     960
gagtgtctgc tattaataac tatgctcaaa aattgtgtac ctttagctttt ttaatttgta   1020 aaggggttaa taaggaatat ttgatgtata gtgccttgac tagagatcat aatcagccat    1080
accacatttg tagaggtttt acttgcttta aaaaacctcc cacacctccc cctgaacctg   1140
aaacataaaa tgaatgcaat tgttgttgtt aacttgttta ttgcagctta taatggttac   1200
aaataaagca atagcatcac aaatttcaca aataaagcat tttttcact gcattctagt    1260 tgtggttttgt ccaaactcat caatgtatct tatcatgtct ggatctgaca tggtaagtaa  1320
gcttgaagtt cctatacttt ctagagaata ggaacttctt taccactccc tatcagtgat   1380
agagaaaagt gaaagtcgag tttaccactc cctatcagtg atagagaaaa gtgaaagtcg  1440
agtttaccac tccctatcag tgatagagaa aagtgaaagt cgagtttacc actccctatc  1500
agtgatagag aaaagtgaaa gtcgagttta ccactcccta tcagtgatag agaaaagtga  1560
aagtcgagtt taccactccc tatcagtgat agagaaaagt gaaagtcgag tttaccactc   1620
cctatcagtg atagagaaaa gtgaaagtcg agctcggtac ccgggtcgag taggcgtgta   1680
cggtgggagg cctatataag cagagctcgt ttagtgaacc gtcagatcgc ctggagacgc  1740
catccacgct gttttgacct ccatagaaga caccgggacc gatccagcct ataacttcgt  1800
atagcataca ttatacgaag ttattgatat cgccaccatg                         1840
```

<210> SEQ ID NO 2
<211> LENGTH: 24
<212> TYPE: DNA
<213> ORGANISM: Artificial Sequence
<220> FEATURE:
<223> OTHER INFORMATION: PCR primer
<400> SEQUENCE: 2
aaattcagga agctgtgtgc ctgc                                            24

<210> SEQ ID NO 3
<211> LENGTH: 24
<212> TYPE: DNA
<213> ORGANISM: Artificial Sequence
<220> FEATURE:
<223> OTHER INFORMATION: PCR primer
<400> SEQUENCE: 3
cggagttgat caccttggac ttgt                                            24

<210> SEQ ID NO 4
<211> LENGTH: 21
<212> TYPE: DNA

```
<213> ORGANISM: Artificial Sequence
<220> FEATURE:
<223> OTHER INFORMATION: PCR primer

<400> SEQUENCE: 4
aggcttgaga tctggccata c                                            21

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
aagggcaaaa gtgagtatgg tg                                           22

<210> SEQ ID NO 6
<211> LENGTH: 25
<212> TYPE: DNA
<213> ORGANISM: Artificial Sequence
<220> FEATURE:
<223> OTHER INFORMATION: PCR primer

<400> SEQUENCE: 6
gcctgcatta ccggtcgatg caacg                                        25

<210> SEQ ID NO 7
<211> LENGTH: 30
<212> TYPE: DNA
<213> ORGANISM: Artificial Sequence
<220> FEATURE:
<223> OTHER INFORMATION: PCR primer

<400> SEQUENCE: 7
aaatccatcg ctcgaccagt ttagttaccc                                   30

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
ttgatcacca aggtgcagag                                              20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
cagggctctt ctcccttctc                                              20

<210> SEQ ID NO 10
<211> LENGTH: 24
<212> TYPE: DNA
<213> ORGANISM: Artificial Sequence
<220> FEATURE:
<223> OTHER INFORMATION: PCR primer

<400> SEQUENCE: 10
agggaatggt ggtctgagtc tgtt                                         24
```

```
<210> SEQ ID NO 11
<211> LENGTH: 24
<212> TYPE: DNA
<213> ORGANISM: Artificial Sequence
<220> FEATURE:
<223> OTHER INFORMATION: PCR primer

<400> SEQUENCE: 11
gagaacaccc atgtcttgta gctg                                            24

<210> SEQ ID NO 12
<211> LENGTH: 30
<212> TYPE: DNA
<213> ORGANISM: Artificial Sequence
<220> FEATURE:
<223> OTHER INFORMATION: PCR primer

<400> SEQUENCE: 12
gttggcgcct accggtggat gtggaatgtg                                      30
```